US011259692B2

(12) United States Patent
Yamamoto

(10) Patent No.: US 11,259,692 B2
(45) Date of Patent: Mar. 1, 2022

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 217 days.

(21) Appl. No.: 16/548,593

(22) Filed: Aug. 22, 2019

(65) Prior Publication Data

US 2019/0374094 A1 Dec. 12, 2019

Related U.S. Application Data

(63) Continuation of application No. PCT/JP2017/046424, filed on Dec. 25, 2017.

(30) Foreign Application Priority Data

Mar. 3, 2017 (JP) .............................. JP2017-040343

(51) Int. Cl.
*A61B 1/04* (2006.01)
*A61B 1/00* (2006.01)
*A61B 1/06* (2006.01)

(52) U.S. Cl.
CPC .......... *A61B 1/041* (2013.01); *A61B 1/00009* (2013.01); *A61B 1/00045* (2013.01);
(Continued)

(58) Field of Classification Search
CPC . A61B 1/041; A61B 1/00009; A61B 1/00045; A61B 1/043; A61B 1/0638; A61B 1/0646; A61B 1/0684
See application file for complete search history.

(56) References Cited

U.S. PATENT DOCUMENTS 8,738,108 B2* 5/2014 Saito ...................... A61B 1/063
600/323
9,095,250 B2* 8/2015 Yamaguchi ........ A61B 1/00009
(Continued)

FOREIGN PATENT DOCUMENTS

EP 1488731 A1 12/2004
EP 2859833 A1 4/2015
(Continued)

OTHER PUBLICATIONS

International Preliminary Report on Patentability and Written Opinion of the International Searching Authority dated Sep. 12, 2019, for International Application No. PCT/JP2017/046424, with an English Translation.

(Continued)

*Primary Examiner* — Timothy J Neal
*Assistant Examiner* — William B Chou
(74) *Attorney, Agent, or Firm* — Birch, Stewart, Kolasch & Birch, LLP

(57) ABSTRACT

An endoscope system 10 includes: an image acquiring unit 54 that acquires an endoscope image obtained by imaging an observation target; a baseline information calculating unit 86 that calculates baseline information by using the endoscope image or a display endoscope image 101 generated by using the endoscope image, the baseline information being information about light scattering characteristics or light absorbing characteristics of the observation target and information that is at least not dependent on particular biological information; an imaging scene determination unit 87 that determines the imaging scene by using the baseline information; and a condition setting unit 88 that sets a condition for imaging or image processing, by using a determination result of the imaging scene determination unit.

20 Claims, 5 Drawing Sheets

(52) U.S. Cl.
CPC ............. *A61B 1/043* (2013.01); *A61B 1/0638* (2013.01); *A61B 1/0646* (2013.01); *A61B 1/0684* (2013.01)

(56) References Cited

U.S. PATENT DOCUMENTS

| | | | | |
|---|---|---|---|---|
| 10,231,658 | B2* | 3/2019 | Shiraishi | A61B 1/04 |
| 10,264,955 | B2* | 4/2019 | Saito | A61B 5/7235 |
| 2002/0026098 | A1* | 2/2002 | Kobayashi | A61B 1/043 600/160 |
| 2010/0208047 | A1* | 8/2010 | Kitamura | G06T 7/11 348/65 |
| 2012/0197076 | A1* | 8/2012 | Minetoma | A61B 5/489 600/109 |
| 2012/0253158 | A1* | 10/2012 | Yamaguchi | A61B 1/0638 600/339 |
| 2015/0238127 | A1 | 8/2015 | Saito | |
| 2016/0058349 | A1* | 3/2016 | Morimoto | A61B 1/0669 600/327 |
| 2016/0379363 | A1* | 12/2016 | Kitamura | A61B 1/0005 600/371 |
| 2017/0014055 | A1 | 1/2017 | Otani | |
| 2017/0296043 | A1 | 10/2017 | On | |
| 2018/0040127 | A1 | 2/2018 | Kanda et al. | |
| 2018/0271412 | A1* | 9/2018 | Shigeta | A61B 5/14552 |
| 2019/0282135 | A1* | 9/2019 | Ito | A61B 1/00006 |

FOREIGN PATENT DOCUMENTS

| | | |
|---|---|---|
| EP | 3005933 A1 | 4/2016 |
| EP | 3427637 A1 | 1/2019 |
| JP | 2010-187756 A | 9/2010 |
| JP | 2011-218090 A | 11/2011 |
| JP | 2013-85593 A | 5/2013 |
| JP | 2015-160013 A | 9/2015 |
| JP | 2015-173827 A | 10/2015 |
| JP | 2017-18503 A | 1/2017 |
| WO | WO 2016/110993 A1 | 7/2016 |
| WO | WO 2016/158276 A1 | 10/2016 |
| WO | WO 2016/170656 A1 | 10/2016 |

OTHER PUBLICATIONS

International Search Report, dated Apr. 3, 2018, for International Application No. PCT/JP2017/046424, with an English translation.
Japanese Office Action for corresponding Japanese Application No. 2019-502477, dated May 6, 2021, with English translation.
Extended European Search Report, dated May 6, 2020, for European Application No. 17898402.7.
Japanese Office Action, dated Oct. 20, 2020, for Japanese Application No. 2019-502477, with an English translation.
European Office Action for European Application No. 17898402.7, dated Mar. 11, 2021.

* cited by examiner

ENDOSCOPE SYSTEM, PROCESSOR DEVICE, AND METHOD FOR OPERATING ENDOSCOPE SYSTEM

CROSS-REFERENCE TO RELATED APPLICATIONS

This application is a Continuation of PCT International Application No. PCT/JP2017/046424 filed on Dec. 25, 2017, which claims priority under 35 U.S.C § 119(a) to Japanese Patent Application No. 2017-040343 filed on Mar. 3, 2017. Each of the above application(s) is hereby expressly incorporated by reference, in its entirety, into the present application.

BACKGROUND OF THE INVENTION

1. Field of the Invention

The present invention relates to an endoscope system that recognizes a part which is being observed or the like, a processor device, and a method for operating the endoscope system.

2. Description of the Related Art

In the medical field, an endoscope system including a light source device, an endoscope, and a processor device is widely used. In recent years, the following endoscope system has been known. The endoscope system not only images an observation target by using the endoscope but also recognizes what kind of observation target is being imaged. For example, an endoscope system described in JP2011-218090A performs processing for identifying a lesion part and a normal part, called type identification processing, and determination of a part of interest and a non-part of interest, called part determination. In addition, a capsule endoscope described in JP2010-187756A identifies the type of an organ in an endoscope image on the basis of color from the following four types: esophagus, stomach, small intestine, and large intestine, and detects a section with a small change in scene from continuous endoscope images so that the endoscope image in the detected section is used for detecting a lesion.

SUMMARY OF THE INVENTION

An endoscope system is required to automatically display an endoscope image that is easily used for diagnosis on a monitor. Thus, the endoscope system needs to determine an imaging scene and set appropriate imaging conditions or perform appropriate image processing so as to generate a display endoscope image. This is because the image quality of the endoscope image may be decreased depending on the imaging scene.

As an image recognition technique, for example, pattern matching is known. However, the determination accuracy of pattern matching is excessive in determination of the imaging scene, which is highly disadvantageous because of a heavy processing load. In addition, when the imaging scene is determined on the basis of color of the endoscope image, the image scene cannot be correctly determined in some cases. For example, the cases include a case where a lesion is present, a case where a treatment tool such as forceps is also imaged, a case where a residue or a residual liquid (hereinafter referred to as a residual liquid or the like) is present, a case where a dye for coloring an observation target is sprayed, a case where bleeding is present, and the like, in which case a part of the observation target has an abnormal color.

An object of the present invention is to provide an endoscope system, a processor device, and a method for operating the endoscope system that enable easier and more robust determination of the imaging scene than in the related art and automatic setting of conditions for imaging or image processing appropriate for the imaging scene.

An endoscope system according to the present invention is an endoscope system including a light source, an endoscope, and a processor device, the endoscope imaging an observation target irradiated with illumination light emitted from the light source, the processor device performing system control and image processing. The endoscope system includes: an image acquiring unit that acquires an endoscope image obtained by imaging the observation target; a baseline information calculating unit that calculates baseline information by using the endoscope image or a display endoscope image generated by using the endoscope image, the baseline information being information about light scattering characteristics or light absorbing characteristics of the observation target and information that is at least not dependent on particular biological information; an imaging scene determination unit that determines an imaging scene by using the baseline information; and a condition setting unit that sets a condition for imaging or image processing, by using a determination result of the imaging scene determination unit.

The imaging scene determination unit preferably determines, as the imaging scene, a type of an observation part, the presence or absence or a type of a lesion, the presence or absence of a treatment tool, the presence or absence of a residue or a residual liquid, the presence or absence of zoom-in, the presence or absence of a dye, or the presence or absence of bleeding.

The condition setting unit preferably sets a kind or a light amount of the illumination light to be used.

The condition setting unit preferably sets the presence or absence or a magnitude of the image processing.

The baseline information calculating unit preferably calculates the baseline information for each part composed of one or more pixels.

The imaging scene determination unit preferably determines the imaging scene of the part composed of one or more pixels, and determines the one imaging scene of the endoscope image or the display endoscope image by using a determination result of the part.

The imaging scene determination unit preferably determines the imaging scene having the largest number in the determination result of the part, as the imaging scene of the endoscope image or the display endoscope image.

If the determination result of the part includes a determination result indicating that the imaging scene is a particular imaging scene, the imaging scene determination unit preferably determines the particular imaging scene as the imaging scene of the endoscope image or the display endoscope image.

The baseline information calculating unit preferably calculates the baseline information by using a plurality of the endoscope images with different kinds of illumination light used for imaging.

The particular biological information is preferably information that changes due to a state of hemoglobin included in the observation target.

The particular biological information is preferably an oxygen saturation or a hemoglobin concentration.

The particular biological information is preferably information about a blood vessel included in the observation target.

The particular biological information is preferably a blood vessel density, a blood vessel depth, or a blood vessel thickness.

A processor device according to the present invention is a processor device that performs system control and image processing of an endoscope system having a light source and an endoscope that images an observation target irradiated with illumination light emitted from the light source. The processor device includes: an image acquiring unit that acquires an endoscope image obtained by imaging the observation target; a baseline information calculating unit that calculates baseline information by using the endoscope image or a display endoscope image generated by using the endoscope image, the baseline information being information about light scattering characteristics or light absorbing characteristics of the observation target and information that is at least not dependent on particular biological information; an imaging scene determination unit that determines an imaging scene by using the baseline information; and a condition setting unit that sets a condition for imaging or image processing, by using a determination result of the imaging scene determination unit.

A method for operating an endoscope system according to the present invention is a method for operating an endoscope system including a light source, an endoscope, and a processor device, the endoscope imaging an observation target irradiated with illumination light emitted from the light source, the processor device performing system control and image processing. The method includes: a step of acquiring, by an image acquiring unit, an endoscope image obtained by imaging the observation target; a step of calculating, by a baseline information calculating unit, baseline information by using the endoscope image or a display endoscope image generated by using the endoscope image, the baseline information being information about light scattering characteristics or light absorbing characteristics of the observation target and information that is at least not dependent on particular biological information; a step of determining, by an imaging scene determination unit, an imaging scene by using the baseline information; and a step of setting, by a condition setting unit, a condition for imaging or image processing, by using a determination result of the imaging scene determination unit.

The endoscope system, the processor device, and the method for operating the endoscope system according to the present invention enable easier and more robust determination of the imaging scene than in the related art and automatic setting of conditions for imaging or image processing appropriate for the imaging scene.

DESCRIPTION OF THE PREFERRED EMBODIMENTS

Figure 1:
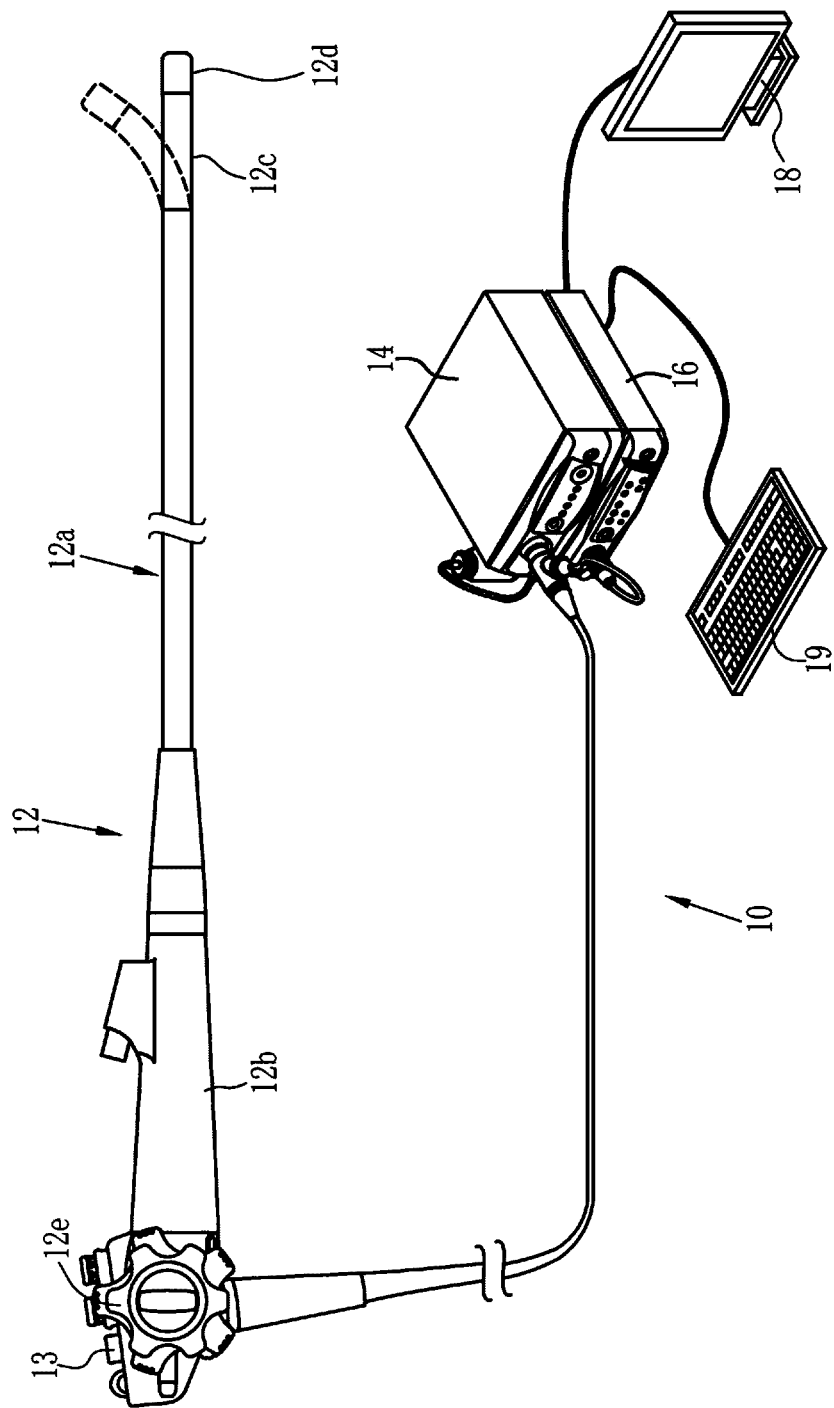
FIG. 1 is an external view of an endoscope system.

As illustrated in FIG. 1, an endoscope system 10 includes an endoscope 12, a light source device 14, a processor device 16, a monitor 18, and a console 19. The endoscope 12 images an observation target. The light source device 14 generates illumination light. The processor device 16 performs system control, image processing, and the like of the endoscope system 10. The monitor 18 is a display unit that displays a display endoscope image generated by the processor device 16. The console 19 is an input device used for inputting settings to the processor device 16, for example.

The endoscope 12 has an insertion part 12a that can be inserted into a subject, an operating unit 12b provided at the base end portion of the insertion part 12a, and a bending part 12c and a tip part 12d provided at the distal end side of the insertion part 12a. Operation of an angle knob 12e of the operating unit 12b causes the bending part 12c to bend. As a result of bending of the bending part 12c, the tip part 12d is oriented in a desired direction. Note that the tip part 12d is provided with an ejection port (not illustrated) through which air, water, or the like is ejected toward the observation target. In addition, the operating unit 12b is provided with a zoom operating unit 13 in addition to the angle knob 12e. Operation of the zoom operating unit 13 causes zoom in or zoom out of the observation target for imaging.

Figure 2:
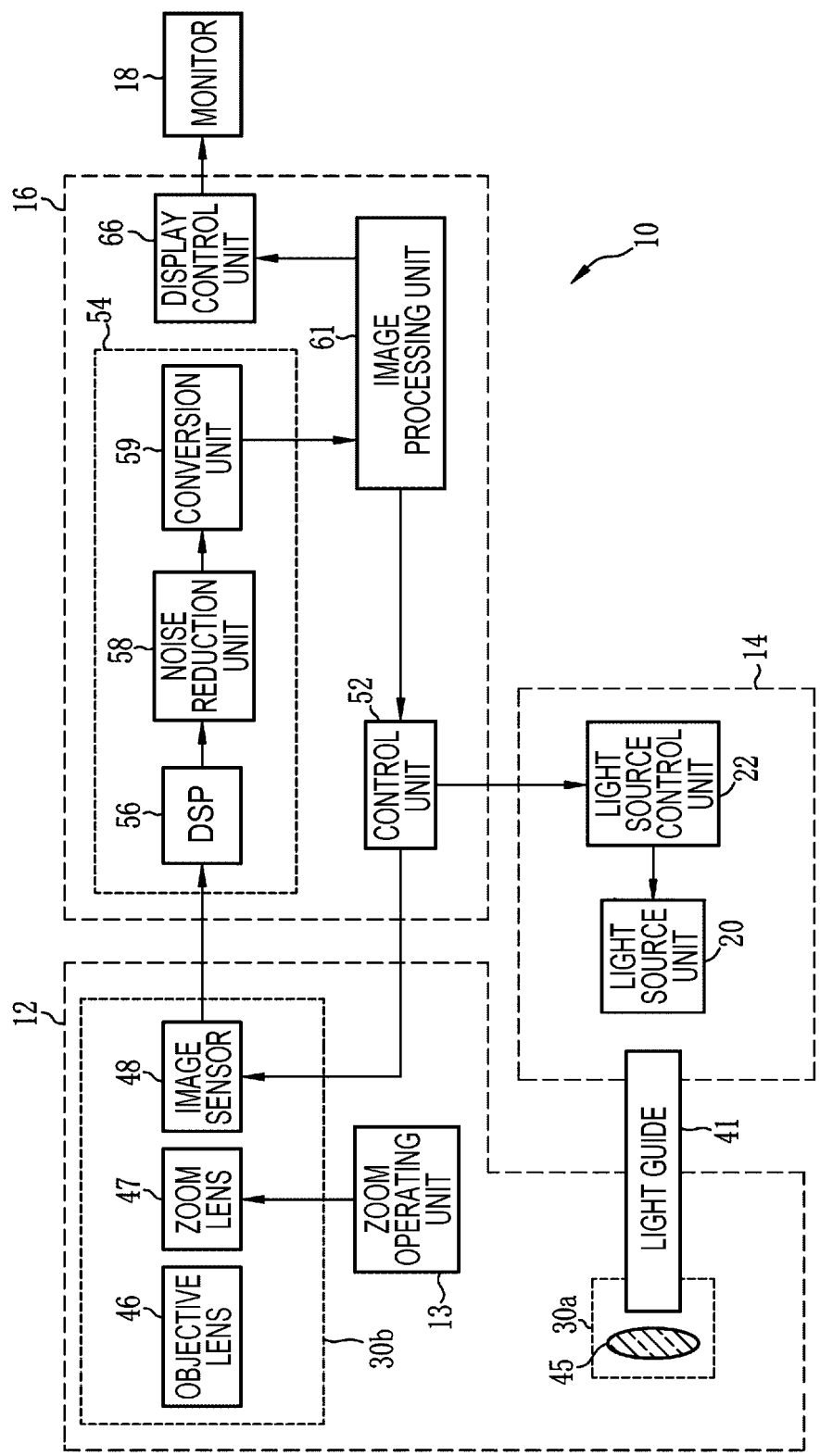
FIG. 2 is a block diagram of the endoscope system.

As illustrated in FIG. 2, the light source device 14 includes a light source unit 20 that emits illumination light and a light source control unit 22 that controls driving of the light source unit 20.

The light source unit 20 includes, for example, a plurality of light emitting diodes (LEDs) that emit light beams with different center wavelengths or wavelength ranges (hereinafter simply referred to as "different wavelengths") as a light source and can emit a plurality of kinds of illumination light with different wavelengths by light emission or turning on of the LEDs, adjustment of light amount, or the like. For example, the light source unit 20 can emit, as the illumination light, each of wide-band violet light, blue light, green light, and red light whose wavelength ranges are comparatively wide. In particular, in addition to the wide-band violet light, blue light, green light, and red light, the light source unit 20 can emit, as the illumination light, narrow-band (the wavelength range is in a range from about 10 nm to 20 nm) violet light, blue light, green light, and red light. More specifically, the light source unit 20 can emit, as the illumination light, narrow-band violet light whose center wavelength is about 400 nm, first narrow-band blue light whose center wavelength is about 450 nm, second narrow-band blue light whose center wavelength is about 470 nm, narrow-band green light whose center wavelength is about 540 nm, and narrow-band red light whose center wavelength is about 640 nm. Besides, the light source unit 20 can emit white light as the illumination light by combining the wide-band or narrow-band violet light, blue light, green light, and red light.

Note that for the light source unit 20, instead of the LEDs, a combination of a laser diode (LD), a fluorescent body, and a band limiting filter, a combination of a lamp such as a xenon lamp and a band limiting filter, and the like can be used. It is needless to say that the fluorescent body or the band limiting filter can be combined and used also in a case where the light source unit 20 is formed of LEDs.

The light source control unit 22 independently controls timings for turning on and off the respective light sources that constitute the light source unit 20, light emission amounts at the time of turning on, and the like. As a result, the light source unit 20 can emit the plurality of kinds of illumination light with different wavelengths. In addition, the light source control unit 22 controls the light source unit 20 in accordance with the timing (so-called frame) of an image sensor 48 for imaging.

Illumination light emitted from the light source unit 20 enters a light guide 41. The light guide 41 is incorporated in the endoscope 12 and a universal cord, and the illumination light propagates therethrough to the tip part 12d of the endoscope 12. The universal cord is a cord connecting the endoscope 12, the light source device 14, and the processor device 16. Note that a multi-mode fiber can be used as the light guide 41. As an example, a small-diameter fiber cable having a core diameter of 105 μm, a clad diameter of 125 μm, and a diameter of Ø 0.3 to 0.5 mm including a protective layer serving as an outer skin can be used. Note that nm represents nanometers, μm represents micrometers, and mm represents millimeters.

The tip part 12d of the endoscope 12 is provided with an illumination optical system 30a and an imaging optical system 30b. The illumination optical system 30a has an illumination lens 45, and an observation target is irradiated with illumination light through the illumination lens 45. The imaging optical system 30b has an objective lens 46, a zoom lens 47, and the image sensor 48. The image sensor 48 images the observation target by using, for example, reflected light (including, in addition to reflected light, scattered light, fluorescence emitted from the observation target, fluorescence caused by medicine that is, for example, administered to the observation target, and the like) of illumination light returning from the observation target through the objective lens 46 and the zoom lens 47. The zoom lens 47 is moved by operating the zoom operating unit 13 and zooms in or zooms out the observation target imaged by the image sensor 48.

The image sensor 48 is, for example, a color sensor having color filters of the primary color system and includes three types of pixels: a B pixel (blue pixel) having a blue color filter; a G pixel (green pixel) having a green color filter; and an R pixel (red pixel) having a red color filter. The blue color filter mainly transmits violet to blue light. The green color filter mainly transmits green light. The red color filter mainly transmits red light. When the observation target is imaged by using the image sensor 48 of the primary color system as described above, three types of images at most, which are a B image (blue image) from the B pixel, a G image (green image) from a G pixel, and an R image (red image) from the R pixel, can be obtained at the same time.

Note that a charge coupled device (CCD) sensor or a complementary metal oxide semiconductor (CMOS) sensor can be used as the image sensor 48. In addition, although the image sensor 48 according to this embodiment is a color sensor of the primary color system, a color sensor of the complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the pixels of the above respective colors when using the color sensor of the complementary color system can be converted into a B image, a G image, and an R image through complementary color-to-primary color conversion. In addition, instead of the color sensor, a monochrome sensor without a color filter can be used as the image sensor 48. In this case, by sequentially imaging the observation target by using illumination light of the respective colors such as BGR, images of the above respective colors can be obtained.

The processor device 16 has a control unit 52, an image acquiring unit 54, an image processing unit 61, and a display control unit 66.

The control unit 52 performs general control of the endoscope system 10 such as synchronization control of an illumination-light irradiation timing and an imaging timing. In addition, if the type, number, or the like of a region that is to be subjected to region determination is set by using the console 19 or the like, the control unit 52 inputs the setting to the light source control unit 22.

The image acquiring unit 54 acquires images obtained by imaging the observation target from the image sensor 48. In this embodiment, since the image sensor 48 has the color filters, the image acquiring unit 54 acquires images of respective colors of illumination light and of respective color filters. An image acquired by the image acquiring unit 54 from the image sensor 48 (image obtained by imaging) and a display image generated by using the image acquired by the image acquiring unit 54 from the image sensor 48 are each an "endoscope image". Hereinafter, unless explicitly distinguished, a simple term "image" means the endoscope image that is obtained by imaging the observation target and is acquired from the image sensor 48, and a simple term "endoscope image" means a display endoscope image 101 (see FIG. 6).

The image acquiring unit 54 has a digital signal processor (DSP) 56, a noise reduction unit 58, and a conversion unit 59, and performs various kinds of processing on the acquired images by using these units, as needed.

The DSP 56 performs various kinds of processing on the acquired images, such as defect correction processing, offset processing, gain correction processing, linear matrix processing, gamma conversion processing, demosaicing processing, and YC conversion processing, as needed.

The defect correction processing is processing for correcting the pixel value of a pixel corresponding to a defective pixel of the image sensor 48. The offset processing is processing for setting an accurate zero level by reducing a dark current component from an image subjected to the defect correction processing. The gain correction processing is processing for adjusting the signal level of each image by multiplying the image subjected to the offset processing by a gain. The linear matrix processing is processing for increasing the color reproducibility of an image subjected to the offset processing, and the gamma conversion processing is processing for adjusting the brightness and saturation of an image subjected to the linear matrix processing. The demosaicing processing (also referred to as isotropic processing or synchronization processing) is processing for interpolating the pixel value of a lacking pixel and is performed on an image subjected to the gamma conversion processing. The lacking pixel is a pixel without a pixel value due to the array of the color filters (because a pixel of another color is arranged in the image sensor 48). For example, since the B image is obtained by imaging the observation target by using the B pixel, there are no pixel values of pixels at positions corresponding to the G pixel and the R pixel. The demosaicing processing interpolates the B image and generates the pixel values of the pixels at positions corresponding to the G pixel and the R pixel in the image sensor 48. The YC conversion processing is processing for converting an image subjected to the demosaicing processing into a luminance channel Y, a chroma channel Cb, and a chroma channel Cr.

The noise reduction unit 58 performs noise reduction processing on the luminance channel Y, the chroma channel Cb, and the chroma channel Cr, by using, for example, a moving average method, a median filter method, or the like. The conversion unit 59 re-converts the luminance channel Y, the chroma channel Cb, and the chroma channel Cr, which have been subjected to the noise reduction processing, into images of BGR colors again.

The image processing unit 61 generates an endoscope image to be displayed on the monitor 18 by using the image acquired by the image acquiring unit 54. In addition, the image processing unit 61 determines an imaging scene by using the image acquired by the image acquiring unit 54 or a display endoscope image generated by using the image acquired by the image acquiring unit 54, and sets conditions for imaging or image processing by using the determination result.

Figure 3:
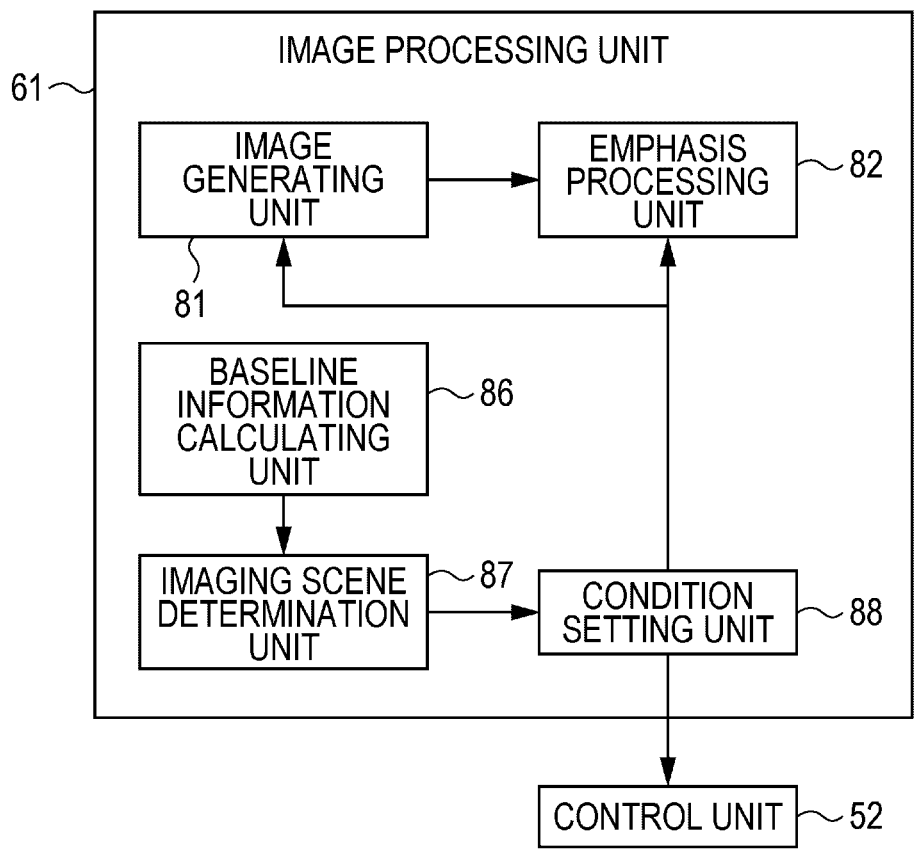
FIG. 3 is a block diagram of an image processing unit.

More specifically, as illustrated in FIG. 3, the image processing unit 61 includes an image generating unit 81, an emphasis processing unit 82, a baseline information calculating unit 86, an imaging scene determination unit 87, and a condition setting unit 88.

The image generating unit 81 generates the display endoscope image 101 by using one or more images acquired by the image acquiring unit 54. When generating the display endoscope image 101, the image generating unit 81 performs, as needed, color conversion processing, hue emphasis processing, and structure emphasis processing on the images acquired by the image acquiring unit 54. In the color conversion processing, the images of BGR colors are subjected to 3×3 matrix processing, gradation transformation processing, three-dimensional look-up table (LUT) processing, and the like. The hue emphasis processing is processing for emphasizing the hue in an image, and the structure emphasis processing is, for example, processing for emphasizing a tissue or a structure of the observation target, such as a blood vessel or a pit pattern.

The emphasis processing unit 82 performs emphasis processing on the endoscope image 101 generated by the image generating unit 81, as needed. For example, the emphasis processing unit 82 performs frequency emphasis processing, edge emphasis processing, brightness adjustment processing, tone change processing, or the like on a part or all of the structure, tissue, or the like of the observation target. The display control unit 66 converts the endoscope image 101 that has been subjected to the emphasis processing by the emphasis processing unit 82 as needed, to a format that is suitable for display and outputs it to the monitor 18. Thus, the monitor 18 displays the endoscope image 101.

The baseline information calculating unit 86 calculates baseline information by using the endoscope image (image acquired by the image acquiring unit 54) obtained by imaging the observation target or the display endoscope image 101 generated by the image generating unit 81. The baseline information is information about light scattering characteristics or light absorbing characteristics of the observation target and is information that is at least not dependent on particular biological information. The term "not dependent" herein means at least a change of the baseline information being larger with respect to the magnitude of the light scattering characteristics or the light absorbing characteristics than with respect to the level of the particular biological information.

The "particular biological information" is, for example, information that changes due to the state of hemoglobin included in the observation target. Specifically, the particular biological information is an oxygen saturation, a hemoglobin concentration, a combination thereof, or the like. In addition, the "particular biological information" is, for example, information about a blood vessel included in the observation target. Specifically, the particular biological information is a blood vessel density, a blood vessel depth, a blood vessel thickness, a combination of two or more of these, or the like.

In this embodiment, the baseline information calculating unit 86 calculates the baseline information by using a plurality of images (endoscope images acquired from the image sensor 48) with different kinds of illumination light used for imaging. In addition, in this embodiment, the baseline information calculating unit 86 calculates baseline information that is at least not dependent on the oxygen saturation. Specifically, an image obtained by imaging the observation target by using the first narrow-band blue light is used as a B1 image, an image obtained by imaging the observation target by using the second narrow-band blue light is used as a B2 image, an image obtained by imaging the observation target by using the narrow-band green light is used as a G2 image, and an image obtained by imaging the observation target by using the narrow-band red light is used as an R2 image. Then, the baseline information calculating unit 86 calculates a ratio of the B1 image to the G2 image (hereinafter referred to as B1/G2), a ratio of the B2 image to the G2 image (hereinafter referred to as B2/G2), and a ratio of the R2 image to the G2 image (hereinafter referred to as R2/G2). Subsequently, an operation value "Z" is calculated according to Formula 1. A phase φ in Formula 1 is defined such that the operation value "Z" is constant with respect to the oxygen saturation of hemoglobin included in the observation target. The phase φ can be obtained in advance by experiment or the like.

$$Z=(B1/G2)\times\cos\varphi-(B2/G2)\times\sin\varphi \qquad \text{[Formula 1]}$$

Figure 4:
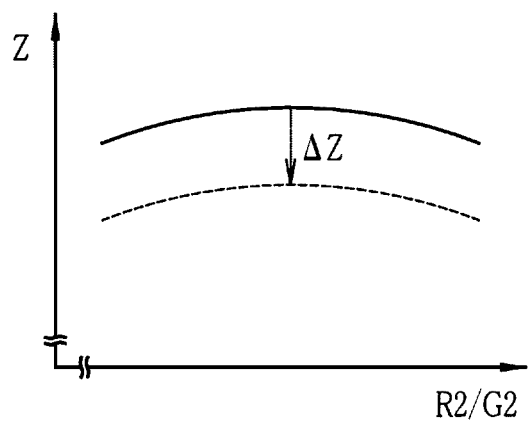
FIG. 4 is a graph illustrating an operation value "Z", which is baseline information.

If there is no residual liquid or the like including a yellow pigment such as bilirubin, as illustrated by the solid line in FIG. 4, the operation value "Z" becomes a fixed value in accordance with the value of the ratio R2/G2, not dependent on the oxygen saturation of the observation target. On the other hand, if there is a residual liquid or the like including a yellow pigment, as illustrated by the broken line, the operation value "Z" varies in accordance with the amount (density) of the yellow pigment included in the residual liquid or the like, although not dependent on the oxygen saturation of the observation target.

The operation value "Z" becomes the fixed value in accordance with the value of the ratio R2/G2 if there is no residual liquid or the like in a case where the observation target actually has light scattering characteristics or light absorbing characteristics that are expected in the adjustment of the phase φ. Thus, in a region in which the observation target actually has light scattering characteristics or light absorbing characteristics that are not expected in the adjustment of the phase φ, or a region in which the observation target seems to have the unexpected light scattering characteristics or the light absorbing characteristics, the operation value "Z" also varies from the fixed value in accordance with the value of the ratio R2/G2 even if there is no residual liquid or the like.

The observation target actually has the unexpected light scattering characteristics or light absorbing characteristics in the adjustment of the phase φ, for example, in a case where the type of an observation part is different, or in a case where a tissue or structure of the observation target is denatured due to a lesion or the like. The types of the observation part include stomach, esophagus, small intestine, large intestine, and the like. In addition, the observation target seems to have the unexpected light scattering characteristics or light absorbing characteristics in the adjustment of the phase φ, for example, in a case where there is a dark part or halation due to the way of irradiation with the illumination light, in a case where a lesion is present, in a case where a treatment tool such as forceps or a stent is present, in a case where the way of irradiation with the illumination light or the like is changed due to a zoom operation or a change in the distance between the tip part 12d and the observation target, in a case where a dye for coloring a tissue or structure of the observation target is administered or sprayed, or in a case where bleeding is present. Thus, the value of the operation value "Z" can be used to determine, in addition to the presence or absence of a residual liquid or the like, the type of the observation part, the presence or absence of a lesion or the type thereof, the presence or absence of a treatment tool, whether zoom-in or zoom-out is performed (hereinafter referred to as the presence or absence of zoom-in), the presence or absence of a dye, the presence or absence of bleeding. It is needless to say that even when the value of the operation value "Z" is changed due to these factors, as long as the phase φ is appropriately adjusted, the operation value "Z" is not dependent on the oxygen saturation.

As described above, the operation value "Z" is "baseline information" that is information about the light scattering characteristics or the light absorbing characteristics of the observation target and that is at least not dependent on the oxygen saturation. Note that the baseline information calculating unit 86 calculates the operation value "Z", which is the baseline information, for each part composed of one or more pixels in an endoscope image. In this embodiment, the baseline information calculating unit 86 calculates the operation value "Z", which is the baseline information, for each pixel.

Although the value of the phase φ is determined such that the baseline information is not dependent on the oxygen saturation in this embodiment, the phase φ may alternatively be determined such that the baseline information is not dependent on the blood vessel density, the blood vessel depth, the blood vessel thickness, or the hemoglobin concentration. In this case, the baseline information calculating unit 86 can calculate the baseline information that is not dependent on the blood vessel density, the blood vessel depth, the blood vessel thickness, or the hemoglobin concentration. Similarly, in a case where the phase φ is adjusted such that the base line information is not dependent on two or more pieces of the "particular biological information" from among the oxygen saturation, the blood vessel density, the blood vessel depth, the blood vessel thickness, and the hemoglobin concentration, the baseline information calculating unit 86 can calculate the baseline information that is not dependent on the two or more pieces of the "particular biological information".

The imaging scene determination unit 87 determines the imaging scene by using the operation value "Z", which is the baseline information. Determination of the imaging scene means, determination of any of the type of the observation part, the presence or absence of a lesion or the type thereof, the presence or absence of a treatment tool, the presence or absence of a residual liquid or the like, the presence or absence of zoom-in, the presence or absence of a dye, and the presence or absence of bleeding, or determination of a combination of these. The imaging scene determination unit 87 determines the imaging scene, for example, for each part composed of one or more pixels, and, by using the determination result of the part, determines one imaging scene of the image acquired by the image acquiring unit 54 or the display endoscope image 101.

For example, if the type of the observation part is different, the value of the operation value "Z" with respect to the ratio R2/G2 (or expected value range), a distribution (or expected distribution range), or a statistic (or expected statistic range), that is, the position, shape, range, or the like of the solid line in FIG. 4 is different. Thus, the type of the observation part can be determined by referring to the actually calculated value of the operation value "Z", the distribution of the operation value "Z", or a statistic such as the average value, the median, or the mode of the operation value "Z". Thus, in a case of determining the type of the observation part as the imaging scene, the imaging scene determination unit 87 determines the type of the observation target for each part composed of one or more pixels, on the basis of the value of the operation value "Z", the distribution of the operation value "Z", or the statistic such as the average value, the median, or the mode of the operation value "Z". Then, among the types of observation parts determined for the respective parts, the type of the observation part having the largest number is determined as the observation part (imaging scene) of the image acquired by the image acquiring unit 54 or the display endoscope image 101.

In addition, in a case where the type of the observation part is known or in a case where it is unnecessary to determine the type of the observation part (e.g., in a case where the observation part is confirmed by other setting or the like), the imaging scene determination unit 87 determines, as the imaging scene, the presence or absence of a lesion or the type thereof, the presence or absence of a treatment tool, the presence or absence of a residual liquid or the like, the presence or absence of zoom-in, the presence or absence of a dye, or the presence or absence of bleeding. Specifically, on the basis of a value $Z_0$ (value on the solid line in FIG. 4) of the operation value "Z" in the actually calculated value of the ratio R2/G2 in a case of a normal observation target without an irregular object, such as a lesion, a treatment tool, a residual liquid or the like, zoom-in, a dye, or bleeding, a change amount $\Delta Z$ ($=Z-Z_0$) of the actually calculated operation value "Z" (value on the broken line in FIG. 4) in the actually calculated value of the ratio R2/G2 is calculated (see FIG. 4). Due to the presence or absence of a lesion or the type thereof, the presence or absence of a treatment tool, the presence or absence of a residual liquid or the like, the presence or absence of zoom-in, the presence or absence of a dye, the presence or absence of bleeding, or the like, the value, the distribution, or the statistic such as the average of the change amount $\Delta Z$ is changed. Thus, by using the value, the distribution, or the statistic of the change amount $\Delta Z$, the imaging scene determination unit 87 determines the cause of the change amount $\Delta Z$ from among the treatment tool, the residual liquid or the like, the zoom-in, the dye, and the bleeding, for each part composed of one or more pixels.

In a case where the determination result of the part includes a determination result indicating a particular imaging scene, the imaging scene determination unit 87 determines the particular imaging scene as the imaging scene of the image acquired by the image acquiring unit 54 or the display endoscope image 101. Specifically, in a case where the image acquired by the image acquiring unit 54 or the display endoscope image 101 includes a predetermined number or a predetermined area of the lesion, the treatment tool, the residual liquid or the like, the zoom-in, the dye, and the bleeding, the imaging scene of the image acquired by the image acquiring unit 54 or the display endoscope image 101 is determined as an imaging scene in which the treatment tool is present, an imaging scene in which the residual liquid or the like is present, an imagine scene that is zoomed in or zoomed out, an imaging scene in which the dye or the like is present, or an imaging scene including bleeding. It is needless to say that in some cases, the imaging scene determination unit 87 determines the imaging scene of the image acquired by the image acquiring unit 54 or the display endoscope image 101 as a complex imaging scene in which two or more of the lesion, the treatment tool, the residual liquid or the like, the zoom-in, the dye, and the bleeding are present.

By using the determination result of the imaging scene determination unit 87, the condition setting unit 88 sets conditions for imaging or image processing. The determination result of the imaging scene determination unit 87 is the imaging scene determined by the imaging scene determination unit 87 for each image acquired by the image acquiring unit 54 or for each display endoscope image 101 and is an imaging scene classified according to the type of the observation part, the presence or absence of a lesion or the type thereof, the presence or absence of a treatment tool, the presence or absence of a residual liquid or the like, the presence or absence of zoom-in, the presence or absence of a dye, the presence or absence of bleeding, or a combination thereof.

The conditions for imaging (hereinafter referred to as imaging conditions) are, for example, the kind (e.g., center wavelength, wavelength range, or shape of spectrum) of illumination light to be used in imaging, the light amount of the illumination light, a combination and balance of light amounts of the illumination light in a case where a plurality of kinds of illumination light are used, an exposure time in the image sensor 48, a gain at the time of image reading, and the like. If the imaging conditions are set by using the determination result of the imaging scene determination unit 87, the condition setting unit 88 inputs the imaging conditions to the units of the light source control unit 22 or the image sensor 48 through the control unit 52.

The conditions for image processing (hereinafter referred to as image processing conditions) are settings as to whether various kinds of image processing are to be performed or not to be performed in the endoscope system 10, the magnitude of various kinds of image processing, and the like. The various kinds of image processing for which the condition setting unit 88 sets the image processing conditions are, for example, the color conversion processing, hue emphasis processing, and structure emphasis processing performed by the image generating unit 81, and the frequency emphasis processing, edge emphasis processing, brightness adjustment processing, tone change processing, and the like performed by the emphasis processing unit 82. In addition, the image processing conditions set by the condition setting unit 88 include settings as to whether various kinds of processing are to be performed or not to be performed by the image acquiring unit 54, the magnitude thereof, and the like. In a case of setting the image processing conditions, the condition setting unit 88 inputs the image processing conditions to the image generating unit 81, the emphasis processing unit 82, or the image acquiring unit 54, as needed.

The condition setting unit 88 stores in advance, for each imaging scene, appropriate imaging conditions, appropriate image processing conditions, or an appropriate combination of imaging conditions and image processing conditions (hereinafter referred to as preset conditions). Thus, the condition setting unit 88 selects preset conditions that are appropriate for the determination result of the imaging scene determination unit 87, and sets the imaging conditions and the image processing conditions according to the selected preset conditions for the light source control unit 22, the image sensor 48, the image generating unit 81, the emphasis processing unit 82, or the image acquiring unit 54. In addition, if the preset conditions are selected, the condition setting unit 88 inputs information regarding the selected preset conditions (hereinafter referred to as preset information) to the display control unit 66. Thus, the display control unit 66 displays the preset information on the monitor 18. Examples of the preset information include the name of the imaging scene corresponding to the preset conditions, the name of the preset conditions, parameters specified by the imaging conditions or the image processing conditions according to the preset conditions, and the like.

Figure 5:
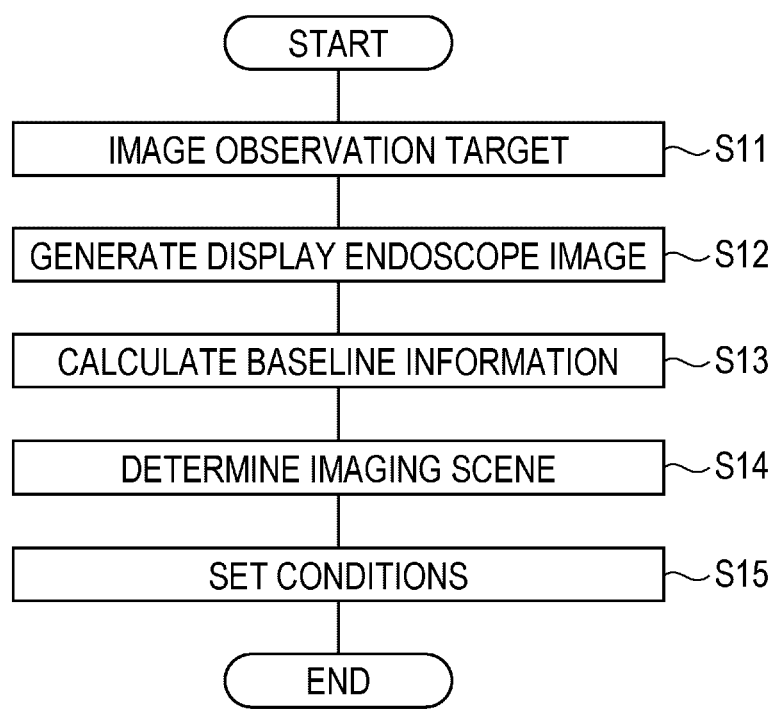
FIG. 5 is a flowchart illustrating the flow of operations of the endoscope system.

Next, the flow of operations of the endoscope system 10 will be described with reference to the flowchart illustrated in FIG. 5. Upon start of observation, the endoscope system 10 images the observation target while switching the illumination light as appropriate (S11). As a result, the image acquiring unit 54 acquires images from the image sensor 48. More specifically, the observation target is imaged while the illumination light is sequentially switched among first illumination light formed of the first narrow-band blue light, second illumination light formed of the second narrow-band blue light, the narrow-band green light, and the narrow-band red light, and third illumination light that is white light. A B1 image can be acquired through imaging using the first illumination light, and a B2 image, a G2 image, and an R2 image can be acquired through imaging using the second illumination light. Images of BGR colors can be acquired through imaging using the third illumination light, which is white light. Hereinafter, the images acquired from a B pixel, a G pixel, and an R pixel through imaging using the third illumination light, which is white light, will be referred to as a B3 image, a G3 image, and an R3 image, respectively.

Figure 6:
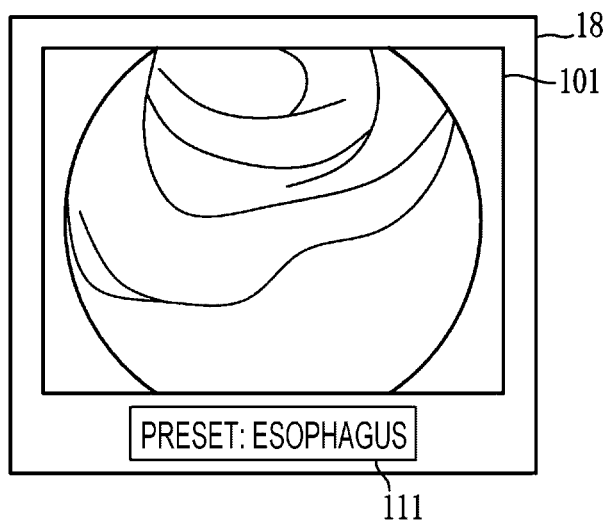
FIG. 6 is an example of display on a monitor.

Upon acquisition of the images of BGR colors in each frame of imaging as described above, the image generating unit 81 generates the display endoscope image 101 by using the B3 image, the G3 image, and the R3 image (S12). Subsequently, the emphasis processing unit 82 performs emphasis processing that is necessary for the display endoscope image 101, and, as illustrated in FIG. 6, the display control unit 66 displays the endoscope image 101 on which the necessary emphasis processing or the like has been performed on the monitor 18.

Upon acquisition of the images of BGR colors in each frame of imaging, the baseline information calculating unit 86 calculates the operation value "Z", which is the baseline information, by using the B1 image, the B2 image, and the G2 image (S13). Then, by using the baseline information, the imaging scene determination unit 87 determines the imaging scene (S14). Subsequently, the condition setting unit 88 selects preset conditions that are appropriate for the determination result of the imaging scene determination unit 87 and sets imaging conditions and image processing conditions according to the selected preset conditions for the light source control unit 22, the image sensor 48, the image generating unit 81, the emphasis processing unit 82, or the image acquiring unit 54 (S15). The display control unit 66 displays the preset information of the selected preset conditions in a preset information display part 111 on the monitor 18 (see FIG. 6).

In the above manner, the endoscope system 10 determines the imaging scene by using the baseline information (the operation value "Z"). The determination of the imaging scene by using the baseline information can be performed with a lighter processing load than in a case where the imaging scene is determined by pattern matching, and at such a high speed that calculation is possible at real time. Furthermore, the determination of the imaging scene by using the baseline information has an accuracy as good as that of pattern matching and has a higher accuracy than the determination of the imaging scene based on the color of the observation target. In addition, the determination of the imaging scene by using the baseline information is less likely to be influenced by a minute structure or the like of the observation target than pattern matching, and thus, the determination of the imaging scene by using the baseline information is more accurate than pattern matching depending on a case. Accordingly, the endoscope system 10 enables easier and more robust determination of the imaging scene than in the related art and automatic setting of conditions for imaging or image processing appropriate for the imaging scene.

In addition, if the imaging scene is determined by using the baseline information, and if the preset setting in accordance with the determined imaging scene is used, and thus, for example, a user does not have to adjust the image quality for each imaging scene. Accordingly, the user's operation load is decreased, and examination time can be shortened. As a result, the user can concentrate on diagnosis in a short time, thereby increasing the accuracy of diagnosis.

Note that the condition setting unit 88 sets the imaging conditions, the image processing conditions, or a combination of the imaging conditions and the image processing conditions in the above embodiment. However, the condition setting unit 88 can set conditions for display (hereinafter referred to as display conditions). For example, if the condition setting unit 88 sets the display conditions in accordance with the imaging scene, the display mode on the monitor 18 can be changed for each imaging scene.

Although the endoscope system 10 generates and displays the endoscope image 101 in the above embodiment, the endoscope system 10 can store the image acquired by the image acquiring unit 54, the display endoscope image 101, or both of them in a storage (including a hospital system connected to the endoscope system 10). In a case where the image acquired by the image acquiring unit 54, the display endoscope image 101, or both of them are stored, the imaging scene determined by the imaging scene determination unit 87, the preset information, and the like are preferably stored in association with the image acquired by the image acquiring unit 54 or the display endoscope image 101. For example, the imaging scene determined by the imaging scene determination unit 87, the preset information, and the like are preferably stored as tag information of the image acquired by the image acquiring unit 54 or the display endoscope image 101.

In the above embodiment, a hardware configuration of a processing unit that performs various kinds of processing is any of the following various processors. Various processors include a central processing unit (CPU) that is a general-purpose processor functioning as various processing units by executing software (programs), a programmable logic device (PLD) that is a processor in which the circuit configuration is changeable after manufacture, such as field programmable gate array (FPGA), a dedicated electric circuit that is a processor having a circuit configuration that is specially designed to execute specific processing, such as an application specific integrated circuit (ASIC), and the like.

One processing unit may be configured from one of these various processors, or may be configured from two or more processors of the same type or different types (e.g., a combination of a plurality of FPGAs or a combination of a CPU and an FPGA). In addition, a plurality of processing units may be configured from one processor.

Furthermore, the hardware configuration of these various processors is, more specifically, electric circuitry obtained by combining circuit devices such as semiconductor devices.

Figure 7:
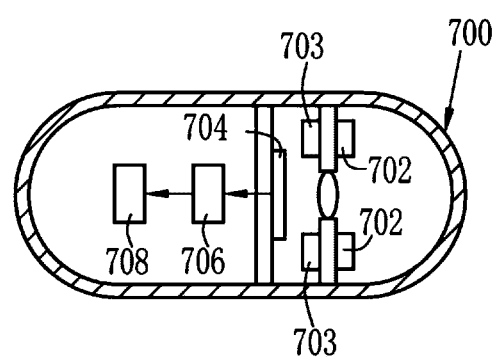
FIG. 7 is a schematic diagram of a capsule endoscope.

Although the present invention is implemented in the endoscope system 10 that performs observation by inserting the endoscope 12 provided with the image sensor 48 into a subject in the above embodiment, the present invention is also suitably used for a capsule endoscope system. As illustrated in FIG. 7, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 serves in the same manner as the light source control unit 22 and the control unit 52. In addition, the control unit 703 can wirelessly communicate with the processor device of the capsule endoscope system by using the transmission/reception antenna 708. The processor device of the capsule endoscope system is substantially the same as the processor device 16 according to the above embodiment, but the image processing unit 706 corresponding to the image acquiring unit 54 and the image processing unit 61 is provided in the capsule endoscope 700, and endoscope images are transmitted to the processor device through the transmission/reception antenna 708. The image sensor 704 is configured in the same manner as the image sensor 48.

REFERENCE SIGNS LIST 10 endoscope system
12 endoscope
12a insertion part
12b operating unit
12c bending part
12d tip part
12e angle knob
13 zoom operating unit
14 light source device
16 processor device
18 monitor
19 console
20, 702 light source unit
22 light source control unit
30a illumination optical system
30b imaging optical system
41 light guide
45 illumination lens
46 objective lens
47 zoom lens
48, 704 image sensor
52, 703 control unit
54, 706 image acquiring unit
56 digital signal processor (DSP)
58 noise reduction unit
59 conversion unit
61 image processing unit
66 display control unit
81 image generating unit
82 emphasis processing unit
86 baseline information calculating unit
87 imaging scene determination unit 88 condition setting unit
101 endoscope image
111 preset information display part
700 capsule endoscope
708 transmission/reception antenna
Z operation value (baseline information)
ΔZ change amount
R2/G2 ratio of R2 image to G2 image

What is claimed is:

1. An endoscope system including a light source, an endoscope, and a processor device, the endoscope imaging an observation target irradiated with illumination light emitted from the light source, wherein
the processor is configured to:
acquire an endoscope image obtained by imaging the observation target;
calculate baseline information by using the endoscope image or a display endoscope image generated by using the endoscope image, the baseline information being information about light scattering characteristics or light absorbing characteristics of the observation target and information that is at least not dependent on particular biological information;
determine an imaging scene by using the baseline information; and
set a condition for imaging or image processing, by using a determination result of the imaging scene, wherein
the processor is further configured to calculate the baseline information by using a plurality of the endoscope images with different kinds of illumination light used for imaging,
wherein
the baseline information is represented by an operation value Z calculated according to Formula 1: [Formula 1]
$Z=(B1/G2) \times \cos \varphi - (B2/G2) \times \sin \varphi$,
where
B1; luminance of an image obtained by imaging the observation target using a first narrow-band blue light,
B2; luminance of an image obtained by imaging the observation target using a second narrow-band blue light,
G2; luminance of an image obtained by imaging the observation target using a narrow-band green light, and
a phase $\varphi$ is defined such that the operation value Z is constant with respect to an oxygen saturation of hemoglobin included in the observation target.

2. The endoscope system according to claim 1,
wherein the processor is further configured to determine, as the imaging scene, a type of an observation part, the presence or absence or a type of a lesion, the presence or absence of a treatment tool, the presence or absence of a residue or a residual liquid, the presence or absence of zoom-in, the presence or absence of a dye, or the presence or absence of bleeding.

3. The endoscope system according to claim 2,
wherein the processor is further configured to set a kind or a light amount of the illumination light to be used.

4. The endoscope system according to claim 2,
wherein the processor is further configured to set the presence or absence or a magnitude of the image processing.

5. The endoscope system according to claim 1,
wherein the processor is further configured to set a kind or a light amount of the illumination light to be used.

6. The endoscope system according to claim 1,
wherein the processor is further configured to set the presence or absence or a magnitude of the image processing.

7. The endoscope system according to claim 1,
wherein the processor is further configured to calculate the baseline information for each part composed of one or more pixels.

8. The endoscope system according to claim 7,
wherein the processor is further configured to determine the imaging scene of the part composed of one or more pixels, and determines the one imaging scene of the endoscope image or the display endoscope image by using a determination result of the part.

9. The endoscope system according to claim 8,
wherein the processor is further configured to determine the imaging scene having the largest number in the determination result of the part, as the imaging scene of the endoscope image or the display endoscope image.

10. The endoscope system according to claim 9,
wherein in a case where the type of an observation part is known or in a case where to determine the type of the observation part is unnecessary,
the determination result of the part is determined, based on the baseline information and a base baseline information,
wherein the base baseline information is information about light scattering characteristics or light absorbing characteristics of the observation target and information that is at least not dependent on particular biological information and obtained in a case where the type of the observation is normal.

11. The endoscope system according to claim 10,
wherein the processor is further configured to determine, on the baseline information and the base baseline information that are calculated, a cause of the change amount from among the treatment tool, a residue, a residual liquid, the zoom-in, a dye, and a bleeding, for each part composed of one or more pixels.

12. The endoscope system according to claim 8,
wherein, if the determination result of the part includes a determination result indicating that the imaging scene is a particular imaging scene, the processor is further configured to determine the particular imaging scene as the imaging scene of the endoscope image or the display endoscope image.

13. The endoscope system according to claim 12,
wherein in a case where number or area of the particular imaging scene is more than a predetermined number or a predetermined area of the treatment tool, of the residue, of the residual liquid, of the zoom-in, of the dye, or of the bleeding, processor is further configured to determine the particular imaging scene as an imaging scene in which the treatment tool is present, an imaging scene in which the residual is present, an imaging scene in which the residual liquid is present, an imagine scene that is zoomed in or zoomed out, an imaging scene in which the dye is present, or an imaging scene including bleeding, respectively.

14. The endoscope system according to claim 1,
wherein the processor is further configured to calculate the baseline information by using a plurality of the endoscope images with different kinds of illumination light used for imaging.

15. The endoscope system according to claim 1,
wherein the particular biological information is information that changes due to a state of hemoglobin included in the observation target.

16. The endoscope system according to claim 15, wherein the particular biological information is an oxygen saturation or a hemoglobin concentration.

17. The endoscope system according to claim 1, wherein the particular biological information is information about a blood vessel included in the observation target.

18. The endoscope system according to claim 17, wherein the particular biological information is a blood vessel density, a blood vessel depth, or a blood vessel thickness.

19. A processor that performs system control and image processing of an endoscope system having a light source and an endoscope that images an observation target irradiated with illumination light emitted from the light source, wherein the processor is configured to:

acquire an endoscope image obtained by imaging the observation target;

calculate baseline information by using the endoscope image or a display endoscope image generated by using the endoscope image, the baseline information being information about light scattering characteristics or light absorbing characteristics of the observation target and information that is at least not dependent on particular biological information;

determine an imaging scene by using the baseline information; and set a condition for imaging or image processing, by using a determination result of the imaging scene, wherein the processor is further configured to calculate the baseline information by using a plurality of the endoscope images with different kinds of illumination light used for imaging, wherein the baseline information is represented by an operation value Z calculated according to Formula 1: [Formula 1]
$Z=(B1/G2)\times\cos \varphi-(B2/G2)\times\sin \varphi$, where B1; luminance of an image obtained by imaging the observation target using a first narrow-band blue light, B2; luminance of an image obtained by imaging the observation target using a second narrow-band blue light, G2; luminance of an image obtained by imaging the observation target using a narrow-band green light, and a phase $\varphi$ is defined such that the operation value Z is constant with respect to an oxygen saturation of hemoglobin included in the observation target.

20. A method for operating an endoscope system including a light source, an endoscope, and a processor, the endoscope imaging an observation target irradiated with illumination light emitted from the light source, the processor performing system control and image processing, the method comprising:

a step of acquiring an endoscope image obtained by imaging the observation target;

a step of calculating baseline information by using the endoscope image or a display endoscope image generated by using the endoscope image, the baseline information being information about light scattering characteristics or light absorbing characteristics of the observation target and information that is at least not dependent on particular biological information, wherein the baseline information is calculated by using a plurality of the endoscope images with different kinds of illumination light used for imaging, the baseline information is represented by an operation value Z calculated according to Formula 1: [Formula 1]
$Z=(B1/G2)\times\cos \varphi-(B2/G2)\times\sin \varphi$, where B1; luminance of an image obtained by imaging the observation target using a first narrow-band blue light, B2; luminance of an image obtained by imaging the observation target using a second narrow-band blue light, G2; luminance of an image obtained by imaging the observation target using a narrow-band green light, and a phase $\varphi$ is defined such that the operation value Z is constant with respect to an oxygen saturation of hemoglobin included in the observation target;

a step of determining an imaging scene by using the baseline information; and a step of setting a condition for imaging or image processing, by using a determination result of the imaging scene.

* * * * *